United States Patent
Botero Rosas et al.

(10) Patent No.: US 11,504,056 B2
(45) Date of Patent: Nov. 22, 2022

(54) METHOD FOR CLASSIFYING ANESTHETIC DEPTH IN OPERATIONS WITH TOTAL INTRAVENOUS ANESTHESIA

(71) Applicant: UNIVERSIDAD DE LA SABANA, Cundinamarca (CO)

(72) Inventors: Daniel Alonso Botero Rosas, Cundinamarca (CO); Oscar Leonardo Mosquera Dussan, Cundinamarca (CO)

( * ) Notice: Subject to any disclaimer, the term of this patent is extended or adjusted under 35 U.S.C. 154(b) by 197 days.

(21) Appl. No.: 16/965,965

(22) PCT Filed: Mar. 22, 2018

(86) PCT No.: PCT/CO2018/000005
§ 371 (c)(1),
(2) Date: Jul. 29, 2020

(87) PCT Pub. No.: WO2019/179544
PCT Pub. Date: Sep. 26, 2019

(65) Prior Publication Data
US 2021/0007660 A1      Jan. 14, 2021

(51) Int. Cl.
*A61B 5/00* (2006.01)
*G16H 50/30* (2018.01)
(Continued)

(52) U.S. Cl.
CPC .......... *A61B 5/4821* (2013.01); *A61B 5/0205* (2013.01); *A61B 5/316* (2021.01);
(Continued)

(58) Field of Classification Search
CPC .......... A61N 5/0618; A61N 2005/0626; A61N 2005/0663; A61N 5/0613; G16H 20/10;
(Continued)

(56) References Cited

U.S. PATENT DOCUMENTS

| 6,315,736 B1* | 11/2001 | Tsutsumi | A61B 5/1106 600/587 |
| 2010/0262377 A1* | 10/2010 | Jensen | A61B 5/4821 702/19 |

(Continued)

FOREIGN PATENT DOCUMENTS

JP      2016140729 A   *   8/2016

OTHER PUBLICATIONS

W. J. Lobato Malaver, C. Fredel Boos and F. M. de Azevedo, "Pattern recognition of epileptiform events in EEG signals using Wavelet Scalograms," 2015 International Conference on BioSignal Analysis, Processing and Systems (ICBAPS), 2015, pp. 123-128, doi: 10.1109/ICBAPS.2015.7292231. (Year: 2015).*

*Primary Examiner* — Brian T Gedeon
*Assistant Examiner* — Joshua Andrew Schum-Houck
(74) *Attorney, Agent, or Firm* — Eugenio J. Torres-Oyola; Victor M. Rodriguez-Reyes; Rafael Rodriguez-Muriel

(57) ABSTRACT

The process for classifying anesthetic depth includes: collecting of biological signals, conditioning of said signals, monitoring of activity of the central and autonomic systems, measurement of indexes and classification of patterns in anesthetic depth. The activity includes: i) Awake: Vigil—Ak. and recovery of verbal response—Rc. ii) Light Anesthesia: Light induction anesthesia—Li. Light recovery—Lr, Light dose, increase in drugs or patient movement (La), iii) General anesthesia: General anesthesia—Ga, one minute after the start of the surgery, and iv) Deep anesthesia: identification of the EEG burst-suppression pattern (BSP) associated with deep anesthesia.

8 Claims, 8 Drawing Sheets

(51) Int. Cl.
  *A61B 5/316* (2021.01)
  *A61B 5/0205* (2006.01)
  *A61B 5/369* (2021.01)
  *A61B 5/318* (2021.01)
  *A61B 5/02* (2006.01)
  *A61B 5/021* (2006.01)
  *A61B 5/024* (2006.01)

(52) U.S. Cl.
  CPC .......... *A61B 5/4035* (2013.01); *A61B 5/4058* (2013.01); *A61B 5/4803* (2013.01); *A61B 5/4839* (2013.01); *A61B 5/726* (2013.01); *A61B 5/7217* (2013.01); *A61B 5/7267* (2013.01); *G16H 50/30* (2018.01); *A61B 5/021* (2013.01); *A61B 5/02028* (2013.01); *A61B 5/02405* (2013.01); *A61B 5/318* (2021.01); *A61B 5/369* (2021.01)

(58) Field of Classification Search
  CPC ........ G16H 70/40; G16H 20/30; G16H 20/70; G16H 50/20; G16H 20/40; G16H 10/20; A61B 5/0002; A61B 5/4809; A61B 5/4812; A61B 5/4815; A61B 5/4836; A61B 5/4848; A61B 5/4806; A61M 21/02; A61M 2021/0044; H04L 67/02; H04L 67/12; H04L 67/42
  See application file for complete search history.

(56) References Cited

U.S. PATENT DOCUMENTS

2016/0235324 A1* 8/2016 Mershin ............... A61B 5/6803
2017/0181693 A1* 6/2017 Kim ....................... A61B 5/316

* cited by examiner

| Confusion Matrix [%] | | | | |
|---|---|---|---|---|
| 99,00 | 1,00 | 0,00 | 0,00 | Awake |
| 4,64 | 87,41 | 7,95 | 0,00 | Ligth Anesthesia |
| 0,00 | 17,54 | 82,46 | 0,00 | General Anesthesia |
| 0,00 | 3,33 | 3,33 | 93,33 | Deep Anesthesia |
| Awake | L. Anesthesia | G. Anesthesia | D. Anesthesia | 90.55% |

METHOD FOR CLASSIFYING ANESTHETIC DEPTH IN OPERATIONS WITH TOTAL INTRAVENOUS ANESTHESIA

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to the field of Physics, specifically to the development of processes and methods for measuring and classifying biological signals according to physical phenomena.

Specifically, the present invention relates to the field of Biomedicine and Neuroscience in the development of processes and methods to monitor, measure and classify anesthetic depth of patients.

The present invention provides an accurate and reliable process for classifying anesthetic depth.

2. Description of Related Art Including Information Disclosed Under 37 CFR 1.97 and 37 CFR 1.98

Monitoring the state of anesthetic depth during surgical procedures with general anesthesia corresponds to one of the current challenges in the field of medicine. The anesthetic depth is usually determined by clinical criteria such as blood pressure, heart rate, body movements, oxygen saturation level and respiratory cycles, and, in some cases, by brain activity monitors that produce an electronic index reflecting the effect of anesthetic drugs.

General anesthesia (GA) is defined as a reversible state induced by drugs characterized by loss of consciousness, amnesia, analgesia and immobility, accompanied by physiological stability and loss of responsiveness, even to painful stimuli. The GA plays a role of great importance in surgical procedures and is also one of the procedures that represent greater risk, since an overdose of the anesthetic agent can induce coma, produce toxicities associated with the type of anesthetic agent or even cause the death of the patient by cardiovascular collapse. On the other hand, a dose lower than that required may give rise to catecholaminergic responses secondary to surgical stimulation, with hypertension, tachycardia and the event known as anesthesia awareness. This can cause the patient to experience sleep disorders, depression, nightmares, generalized anxiety, fear of hospitals, and to develop post-traumatic stress disorder. In this context, it is important to monitor anesthetic depth, which refers to the continuous tracking of the progressive depression of the Central Nervous System (CNS) and the decrease in the ability to respond to stimuli, for which the Autonomic Nervous System (ANS) is important.

In order to quantify and extract information from these systems, Digital Signal Processing (DSP) techniques are generally studied to analyze the information contained in biological signals of the central and autonomic nervous systems, and they are mainly used to quantify the degree of disorder-complexity in biological signals, especially in the analysis of brain waves, which are characterized by a pattern in the time domain that is not very predictable and of high complexity. The study of these techniques provides the fundamental tools for the development of processes and the implementation of new technologies in the monitoring of anesthetic depth.

Particularly, the patent application EP 1757226 discloses a method and apparatus for measuring the responsiveness of a subject with a reduced level of consciousness. From physiological signal data, a first measure indicative of the level of consciousness of the subject is obtained. In order to obtain an objective measurement of the subject's responsiveness and to improve the specificity of the patient's monitoring, a sequence of the first measurement without inducing awakenings is registered and a second measurement as indicative of a subject's responsiveness according to the recorded sequence is made. The determination of the second measurement can be independent of the unintentional stimuli that cause awakenings to the patient or the stimuli that cause such awakenings in the clinical environment can be detected to know their effect on the first measurement.

In turn, the patent application U.S. Pat. No. 5,372,140 discloses a method and apparatus for providing a measurement of the depth of anesthesia. In this invention, a series of R waves are analyzed using circular statistics to derive a length of the measurement vector that represents the R in the sample. The Rayleigh Test is applied to determine a reference vector length from a predetermined probability level and the number of R waves in the analyzed series. The length of the measurement vector is compared with the length of the reference vector to derive a measurement of the completion of the anesthesia.

The patent application US 2012277548 also discloses methods and systems incorporating nonlinear dynamic analysis (NDA) such as entropy or other complexity analysis and monitoring of continuous signals or evoked potentials of a biological subject, in which said system comprises stages of processing that include the combination of an evoked biological signal as a result of the stimulation of a patient and a nonlinear analysis method capable of capturing temporal changes in order of a signal or its regularity, any combination of evoked processes or peripheral or central nervous physiological mechanisms, a means to generate a measure indicative of the level of anesthesia and consciousness depth (A&CD), sedation or sleep/awakening of a patient's status. These methods and systems incorporating a NDA improve discrimination between sources of different signals, including any combination of the central nervous system (CNS). peripheral nervous system (PNS), autonomic nervous system (ANS), awakenings and artifacts.

Other more recent patent applications, such as US 20150208926, disclose a method and apparatus for estimating the depth of anesthesia, which includes the steps of acquiring an ECG signal, the quantification of the regularity of the respiratory sinus arrhythmia (RSA) from the ECG signal to obtain an index and the estimation of the depth of the anesthesia in function of said index.

The present invention provides a process that includes an index of anesthetic depth monitoring that considers the changes in the activity patterns of the central and autonomic nervous systems and integrates the information extracted from these systems in order to classify the state of depth.

BRIEF SUMMARY OF THE INVENTION

The present invention relates to a process for classifying anesthetic depth comprising the following stages: Collection of biological signals, conditioning of biological signals, monitoring of the activity of the central and autonomic nervous systems, measurement of indexes and classification of anesthetic depth patterns.

In its most general aspect, in the process of the present invention, the collection of biological signals includes the collection of electroencephalogram (EEG), electrocardiogram (ECG) and mean non-invasive blood pressure (NIBPm). In the conditioning of these signals, the elimination of artifacts external to the patient and of biological noise is carried out through the application of a digital bandpass filter and wavelet threshold filter. In the monitoring of the CNS and ANS activity, the complexity of the EEG signal is measured with information entropy methods and the development of the CBI (Complexity Brainwave Index), and the integration with the heart rate variability (HRV) measurement methods is performed: CVI (Cardiac Vagal Index), CSI (Cardiac Sympathetic Index) derivatives of the ECG signal. Then, the classification of patterns associated with the CNS, ANS, and blood pressure is performed. According to the response measurements of the indexes to clinical events during the surgical procedure, the design of pattern classifiers is made and, finally, the classification of the patient's status in anesthetic depth is performed.

DETAILED DESCRIPTION OF THE INVENTION

The present invention relates to a process for classifying anesthetic depth comprising the stages: Collection of biological signals, conditioning of biological signals, monitoring of biological signals, measurement of indexes and classification of patterns in anesthetic depth.

Collection of Biological Signals

Figure 1:
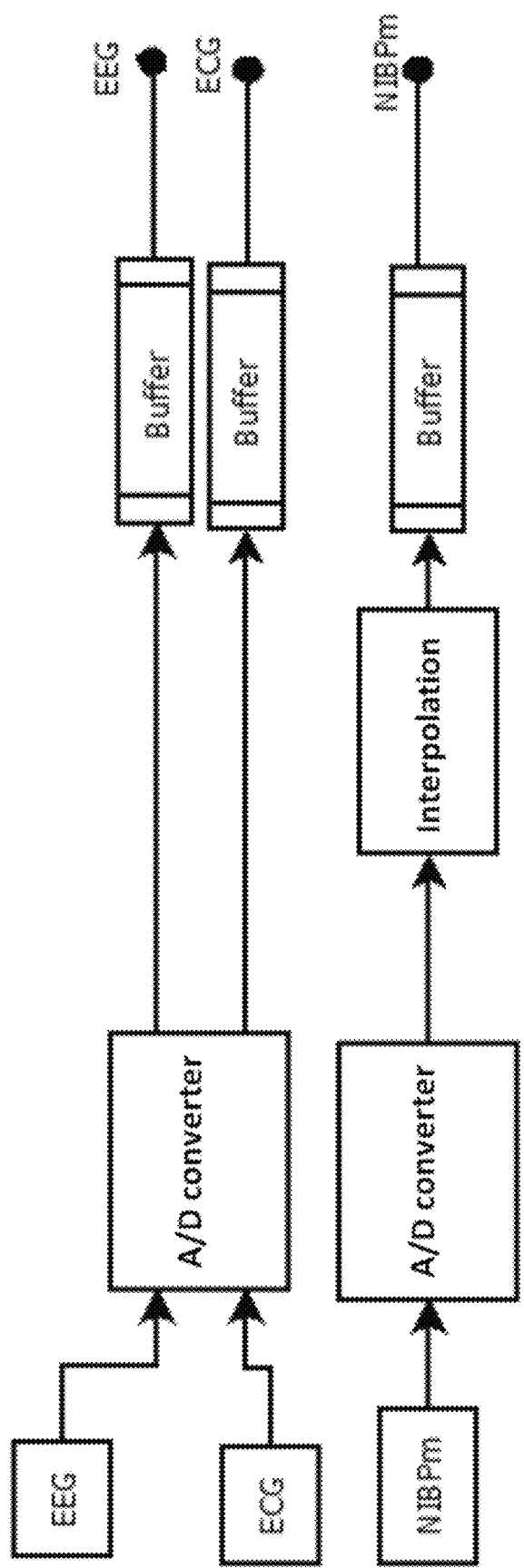
FIG. 1 is a schematic view showing a collection of biological signals and buffer storage of 1024 samples.

In one aspect of the invention, the Electroencephalogram (EEG) and Electrocardiogram (ECG) signals are collected at a sampling frequency of 100 to 500 Hz and the mean non-invasive blood pressure (NIBPm) is recorded at intervals of [150 to 300 s]. The signals are digitized with an ADC (Analog/Digital Converter) of 12-16-bit resolution. FIG. 1 shows a block diagram of this stage.

Conditioning of Biological Signals

In this same aspect of the invention, in the signal conditioning stage, digital filters are implemented for EEG (bandwidth, [0.5-47 Hz]), to avoid noise in the power line (50 o 60 Hz) and, in general terms, high frequency contamination due to external sources and surgical instruments. Then, a threshold technique in wavelet components is applied. The discrete stationary wavelet transform from 4 to 8 levels with coiflet-3 as mother wavelet is applied to epochs of EEG recordings without apparent contamination and epochs of EEG with artifacts in frequency bands of the wavelet decomposition component in frequency ranges according to the levels depending on the sampling frequency of the biological signals. The wavelet coefficients of each level greater than a threshold (average plus two standard deviations of non-contaminated epochs) take values of zero, which is equivalent to subtracting in time, point to point, the contaminant signal, associated to the wavelet coefficient that exceeds the threshold.

Figure 2:
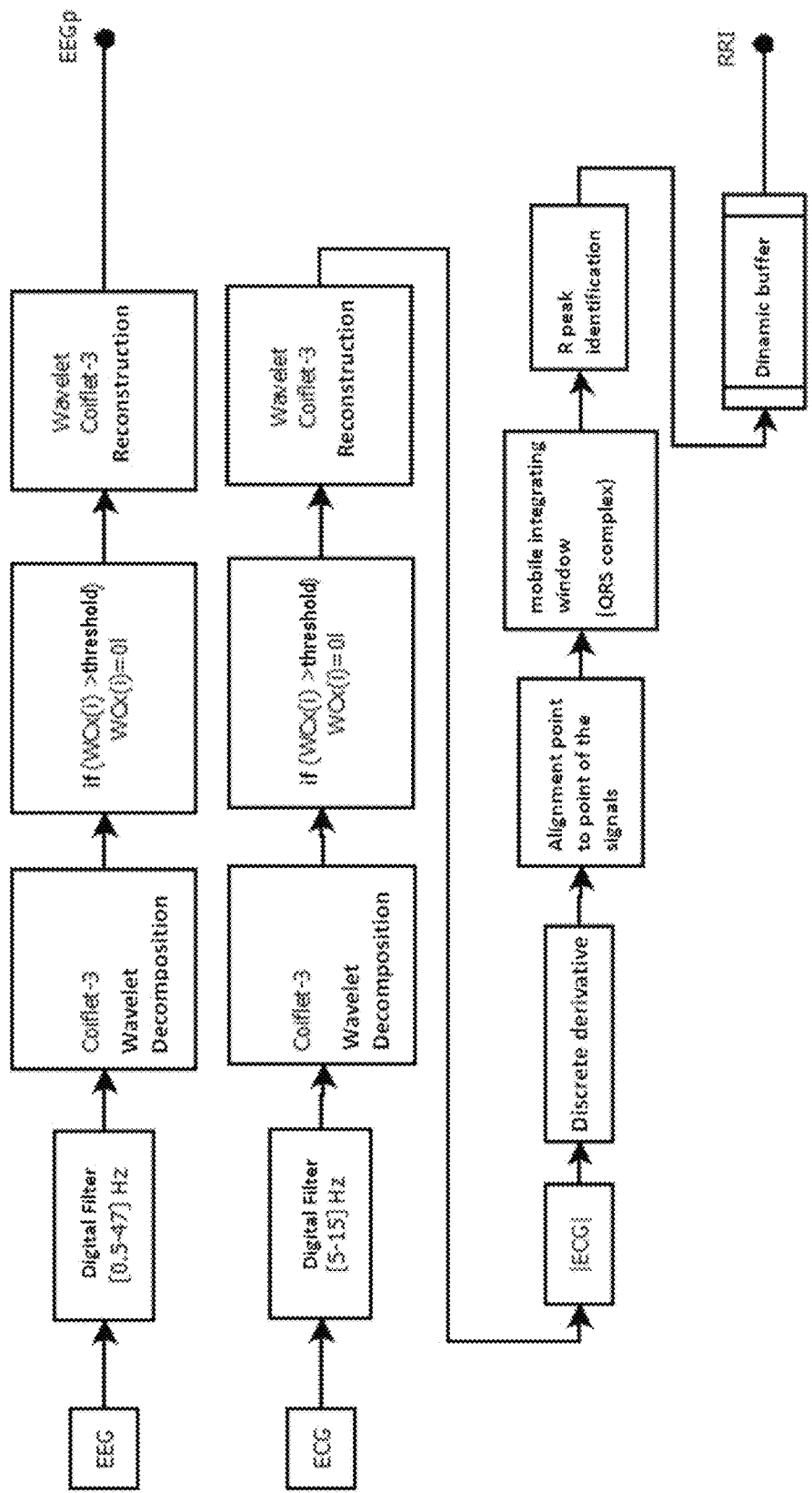
FIG. 2 is a schematic view of conditioning of the EEG signal with digital filter, and wavelet threshold method.

Also, to determine the heart rate variability (HRV), a conditioning of the ECG signal is performed to obtain the temporal series of intervals between beats. These stages include digital filtering (bandwidth, [5-15 Hz]), filtering by wavelet thresholds, a non-linear transformation and the application of decision rule, by which the QRS complex of the T wave is discriminated in consideration of the value of the slope, with the slope in the QRS complex being higher. With this processing, muscle activity noise, power line interference (50 or 60 Hz), baseline deviation and influence of the T wave are reduced. The energy of the QRS complex is distributed mainly between 5-15 Hz in the frequency spectrum. This is the bandpass desired and implemented in the digital filter. The non-linear transformation applied corresponds to a point-to-point amplification of the filtered signal to obtain the square of it. The time series formed by the R peak intervals (RRI) constitute the biological signal for the measurement of HRV, from which indexes of autonomic activity of the patient during a surgical procedure are developed. FIG. 2 shows, in a block diagram, the processes performed to obtain artifact-free signals that reflect the biological significant information.

In particular, the RRI heart rate variability series is obtained from conditioning the ECG signal with digital filter, wavelet threshold method, QRS complex detection and dynamic buffer storage (variable length).

Monitoring of Biological Signals

In this same aspect of the invention, the monitoring of the activity of the central and autonomic nervous systems corresponds to the extraction and identification of patterns of the information contained in the biological signals. Changes in the complexity of the EEG time series are monitored with the CBI constructed from sample entropy (SampEn) and permuted entropy (PE).

For this follow-up, a single processing of the signals that is defined in several clinical events is previously performed: 1. Activity in wakefulness (Ak): Signal corresponding to 30 seconds prior to the induction of TIVA; 2. Light anesthesia (Li): Corresponding to the mean time between the induction of anesthesia and the start of airway management; 3. General anesthesia (GA): Corresponding to one minute after starting the surgical procedure; 4. Deep anesthesia (Bs): Identification of the Burst-Suppression pattern (BSP) in the EEG signal. Interspersed periods of low amplitude (<5 uV) with bursts of EEG activity are the main characteristics of this pattern; 5. Light Recovery (Lr): Identified as the intermediate point between the suspension of drugs via TCI pump and extubation of the patient; 6. Recovery of verbal response (Rc): Identified 30 seconds after the extubation of the patient.

Likewise, in order to measure the sample entropy (SampEn), the definition and quantification of two parameters—the pattern length ($m_1$) and the similarity criterion (r)—are analogously done. The PE requires the definition of the pattern length ($m_2$) and a delay parameter (tau). In addition, combinations of the parameters are tested (m=[2 3 4 5 6], r=[0.1 0.15 0.25 0.30 0.35]) times the standard deviation of the epoch under observation, tau=[1 2 3 4 5]).

In this aspect of the invention, the results of the application of the previous processing show that the permuted entropy provides a greater probability of classification in general terms, but fails when it has to quantify the BSP pattern in the EEG associated with deep anesthesia. On the other hand, sample entropy provides, in general terms, a lower probability of classification, but it is a good measure of complexity to predict deep anesthesia and quantify the BSP pattern.

Therefore, in this same aspect of the invention, the monitoring of PE and SampEn measurements is included as complementary measures to quantify the complexity changes in the EEG record. Both measures are combined in an index called the Complexity Brainwave Index (CBI). The PE determines the behavior of the index in the induction phase. Once the PE value is lower than the median of the values associated with the Ga event, indicating that the patient is under general anesthesia, the SampEn measurement is activated to predict deep anesthesia states and it determines the index response.

The CBI is postprocessed to provide a set of operating points between 0 and 100. A higher prediction probability value is obtained with the combination of both complexity measures. The advantages of both measures are exploited in the CBI. The PE determines the behavior of the CBI most of the time, but when the SampEn provides a low value of complexity and predicts a deep anesthesia state (BSP), the response of the CBI is determined by the SampEn.

Figure 3:
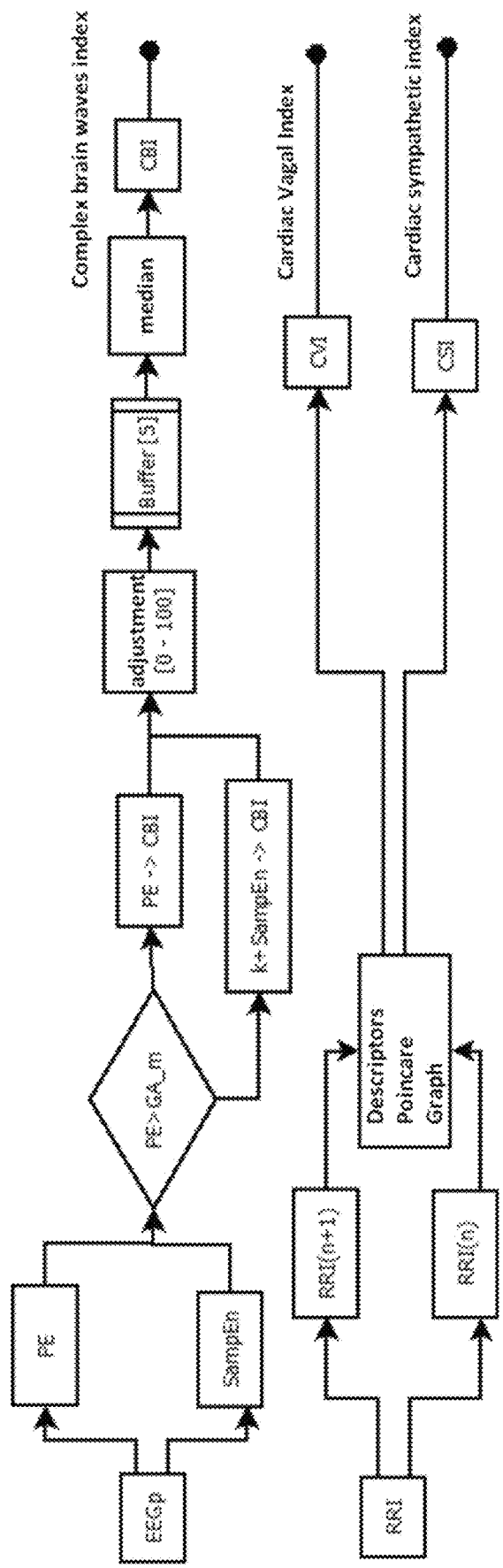
FIG. 3 is a schematic view of monitoring of EEGp and RRI signals. CBI measures brain electrical activity associated with the central nervous system and patient consciousness. CVI and CSI measure the vagal and sympathetic response associated with the autonomic nervous system, responsiveness and nociception.

Autonomic nervous system behavior is measured with the Cardiac Vagal Index (CVI) and the Cardiac Sympathetic Index (CSI) which derive from the descriptors SD1, SD2 of the Poincare-Lorentz chart pattern of the RRI series. FIG. 3 shows the monitoring diagram from the previous processing of the signals.

In this aspect of the invention, the CVI and CSI measure the vagal and sympathetic response associated with the autonomic nervous system, responsiveness and nociception.

In addition to the clinical events previously described in the process of the invention, the event of Light Dose—La is also defined, composed of those epochs in which it occurred: i) An increase in the initial dose (Pf=2.5 µg/ml, Rf=5 µg/ml) of the opioid remifentanil individually or together with propofol in the 30 minutes after the last adjustment of anesthetic drugs by an increase in target concentration in effect site or via intravenous bolus administration; ii) Movement of the patient during the surgical procedure.

In this same aspect of the invention, the BSP pattern was presented in 10% of the sample and the occurrence of five non-consecutive epochs was taken to better characterize the state of deep anesthesia.

Figure 4:
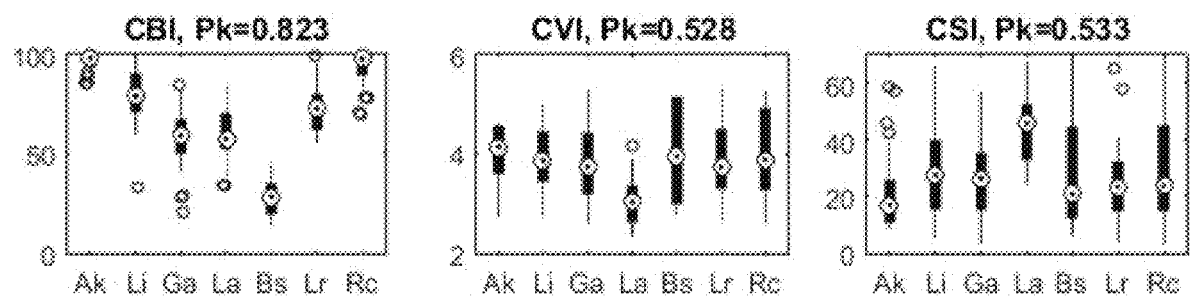
FIG. 4 is a schematic view of a box plot for CBI, CVI and CSI values in each of the previously defined clinical events (Ak, Li, Ga, La. Bs, Lr, Rc).

FIG. 4 shows that the CBI provides the best prediction probability (Pk=0.823) and is an indicator sensitive to transitions between clinical events, but presents problems between the Ga and La events.

The events are usually identified during the surgical procedure in response to nociceptive stimulation, when the expected state of the patient is that of the clinical event Ga, so the pairing prediction probability between La and Ga was considered important and was also estimated for each indicator, as well as the probability of prediction paired between La and the other clinical events, as shown in Table 1.

In this aspect of the invention, for this data, PKm corresponds to the mean prediction probability value for each indicator.

In this aspect of the invention, for this data, PKm corresponds to the mean prediction probability value for each indicator.

TABLE 1

Pairing prediction probability between events for the CBI, CVI and CSI.

| Predictor-La | Pairing $P_K$ | | | | | | |
|---|---|---|---|---|---|---|---|
| | Ak | Li | Ga | Da | Lr | Rc | $P_{Km}$ |
| CBI-La | 0.97 | 0.89 | 0.53 | 0.98 | 0.694 | 0.98 | 0.83 |
| CVI-La | 0.88 | 0.86 | 0.8 | 0.86 | 0.84 | 0.81 | 0.84 |
| CSI-La | 0.93 | 0.81 | 0.82 | 0.86 | 0.87 | 0.78 | 0.85 |

With the application of the process of the invention, it is established that, in general terms, the index derived from the analysis of the EEG signal (CBI) presents a better classification functionality to establish anesthetic depth states, but presents problems with the clinical event La, associated with the state of light anesthesia. On the other hand, the CVI and CSI show a low performance in general terms, but present a good performance to differentiate the clinical event of light dose La from all others, including Ga.

Figure 5:
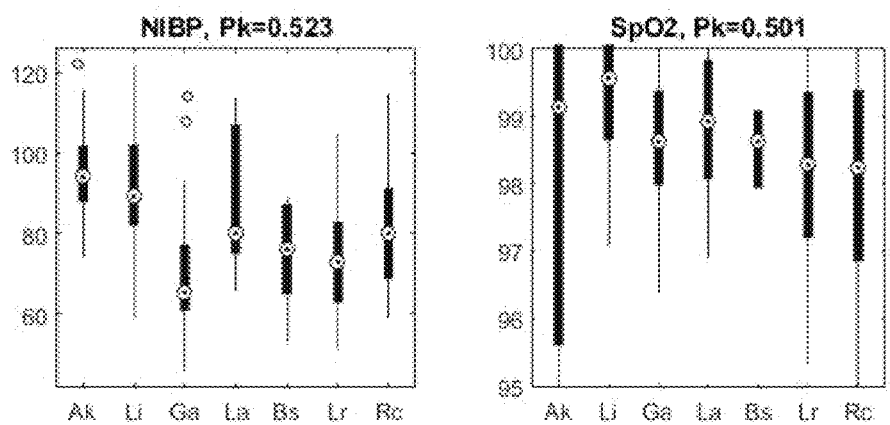
FIG. 5 is a schematic view of Mean NIBP and $SpO_2$ values in previously defined clinical events. It can be noted that the $SpO_2$ was greater than 95% for all events, and that the NIBP tends to increase in the L and La events.

In the process of the invention, it is noticed that the NIBPm increases in La compared to Ga as shown in FIG. 5, which is expected since the NIBPm is well-known by anesthesiologists as an important indicator when adjusting dose of anesthetic drugs.

In this aspect of the invention, it can be noticed that the SpO2 was greater than 95% for all events, and that the NIBPm tends to increase its value in events Li and La with respect to Ga, Bs, Lr, Rc.

Classification of Patterns

The anesthetic depth pattern classification in the process of the invention is carried out in accordance with the implementation of an artificial intelligence method and supervised learning of patterns in CBI, CVI, CSI, and NIBPm indexes. These indexes were selected for the predictive potential of anesthetic depth state when integrated.

In this stage of the invention, a multilayer feedforward neural network is designed with an output layer in which a neuron is associated by state of anesthetic depth to classify with normalized exponential activation function, which is ideal for the type of output of the neural network. With respect to the inputs, the response is of exponential type with a maximum value of 1. The neurons of the hidden layer have a hyperbolic tangent activation function. The number of neurons in this layer is chosen in a way that minimizes the classification error in cross-validation with 5 partitions.

Figure 6:
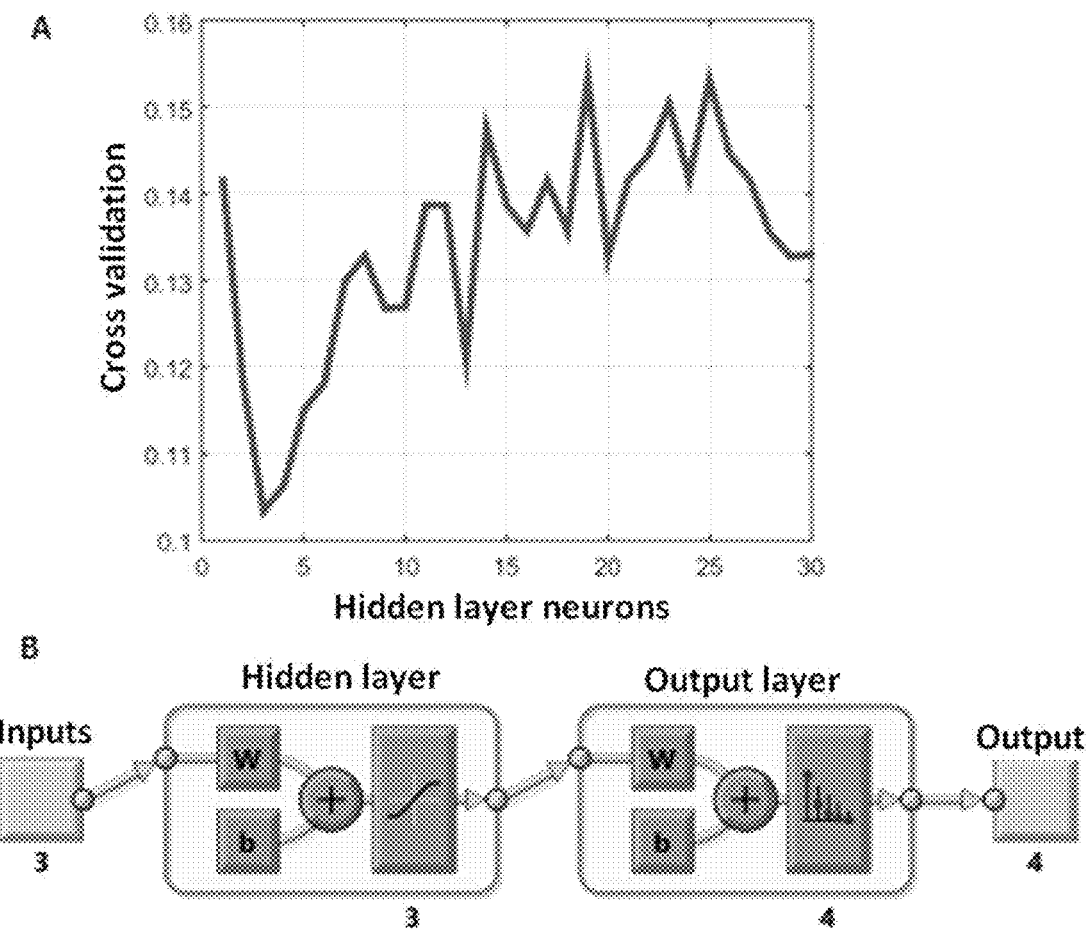
FIG. 6 is a graph illustration and schematic view of outline and cross-validation of the artificial neural network (ANN). It is observed that the number of neurons n=3 in the hidden layer minimizes the cross validation error.

In this same aspect of the invention, once the respective cross-validation of the ANN is trained and performed and the generalization capacity has been analyzed, this is applied to determine the patient's status. FIG. 6 shows the scheme and the cross-validation of the ANN.

In this same aspect of the invention, in the pattern classification stage, cross entropy (xE) is measured as the performance function of ANN during training thereof. The neural network is trained with backpropagation of the scaled conjugate gradient (SCG).

In particular, this technique can train any ANN in which weights, network inputs and activation functions are derivable. The basic backpropagation algorithm adjusts the weights and bias of the ANN in the steepest descent direction (negative of the gradient). This is the direction in which the mean value of xE is decreasing most rapidly.

More particularly, it turns out that, although the function decreases most rapidly along the negative of the gradient, this does not necessarily produce the fastest convergence. In the conjugate gradient algorithms, a search is performed along conjugate directions, which generally produces faster convergence than steepest descent directions. The SCG has shown to be considerably faster than the standard backpropagation classification of the descending gradient.

Figure 7:
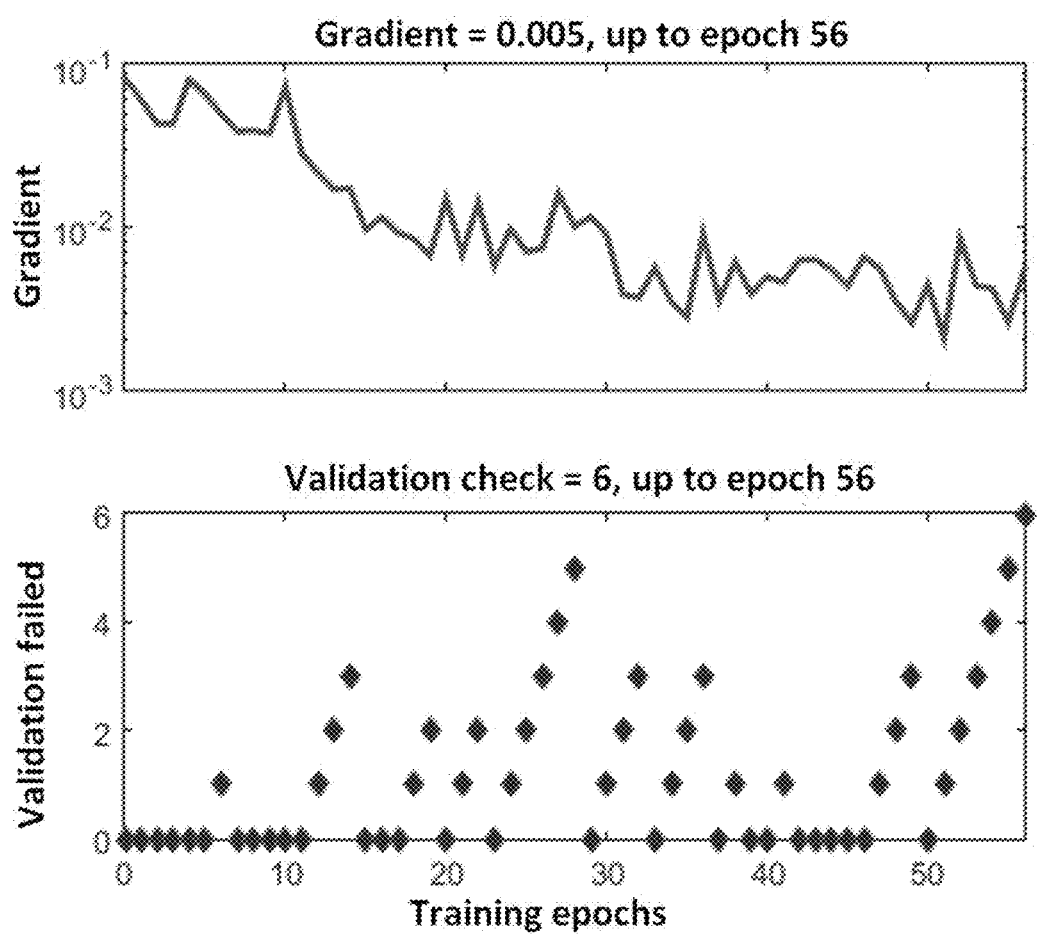
FIG. 7 are graph illustrations of ANN training, scaled conjugate gradient and verification of validation.

The training of ANN is shown in FIG. 7. It stops when one of these conditions occurs: the maximum number of training epochs is reached, the magnitude of the gradient of the performance function is less tan $1 \times 10^{-5}$, or the number of validation verifications is equal to 6. This corresponds to the number of successive validations in which the performance error of the ANN fails to decrease.

In this same aspect of the invention, the training of the neural network involves a random initialization of the synaptic and bias weights. Depending on the same randomness, it is possible to obtain a better or worse performance of the network. This phenomenon can be thought of as the network's predisposition for learning. The adjusted ANN in each of the cross-validation partitions was randomly initialized and trained 30 times. Particularly, in each partition, 30 "versions" of the trained ANN are obtained. The error of the cross validation for each partition is the average of the fifth part that represents the best versions of the ANN.

Particularly, once the training of the ANN is completed, the classification error is estimated since, ultimately, this is the value of interest to evaluate the behavior of the pattern classifier. The performance of the neural network according to the predictors used is shown in Table 2.

TABLE 2

Performance of the network. CE: classification error, X-Val: cross-validation error in 5 partitions. The best performing ANN is in bold.

| Predictors | Neurons in a hidden layer | CE | X-Val |
| --- | --- | --- | --- |
| CBI,CVI | 3 | 0.109 | 0.115 |
| CBI,CSI | 6 | 0.106 | 0.112 |
| CBI,NIBP | 3 | 0.127 | 0.130 |
| CBI,CVI,CSI | 5 | 0.103 | 0.112 |
| CBI,CVI,NIBP | 3 | 0.097 | 0.103 |
| CBI,CSI,NIBP | 6 | 0.100 | 0.112 |
| CBI,CVI,CSI,NIBP | 3 | 0.103 | 0.121 |

Figure 8:
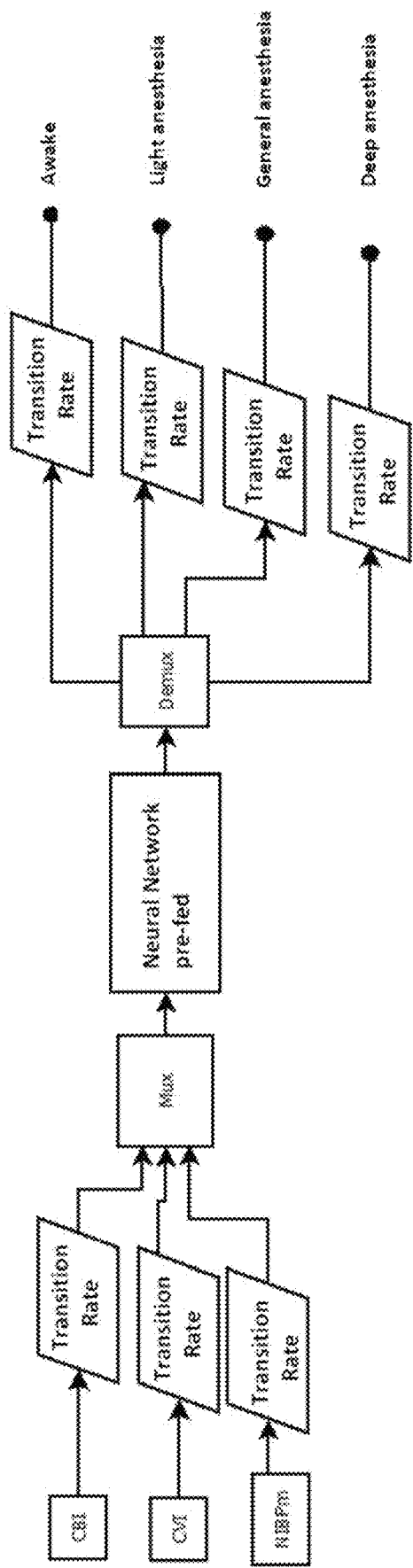
FIG. 8 is a schematic view of multilayer feed-forward artificial neural network implemented. The indexes (CBI. CVI) and NIBPm are multiplexed to feed the network and demultiplexed to provide the patient's status. Transition rates are used to synchronize the entries and responses of the ANN.

FIG. 8 illustrates the artificial intelligence method designed to classify patterns in the CBI, CVI, and NIBPm measurements. Four states of the patient associated with each ANN response neuron are defined: a.) Awake: Vigil—Ak, and recovery of verbal response—Rc.; b.) Light anesthesia: Light induction anesthesia—Li, Light recovery—Lr, Light dose—La; c.) General anesthesia: General anesthesia—Ga, one minute after the start of the surgery; d.) Deep anesthesia: identification of the EEG burst-suppression pattern (BSP) associated with deep anesthesia. Transition rates are applied to synchronize the inputs and responses of the ANN.

Preferred Embodiments

In the preferred embodiment of the present invention, the collection of biological signals is performed by recording the brain electrical activity (EEG), using the unilateral reference sensor with a scanning electrode in the FT10 position (frontotemporal area) and a reference electrode in the FPz position (frontopolar area). Likewise, the collection of biological signals is performed by recording the cardiac electrical activity (ECG), using an assembly with three leads. In this same preferred aspect, EEG and ECG are sampled at 300 Hz, NIBPm values are recorded every 150 s (0.0067 Hz) and then the NIBPm data are interpolated to obtain a uniform sampling of the signals.

In the preferred embodiment of the present invention, the conditioning of said signals is carried out by applying a digital filter with a bandpass between 0.5 and 47 Hz, in order to avoid noise in the power line (50 o 60 Hz) and, in general terms, high frequency contamination due to external sources and surgical instruments. Subsequently, the threshold technique in wavelet components is applied. The discrete stationary wavelet transform of 6 levels, with coiflet-3 as mother wavelet is applied to epochs of EEG recordings without apparent contamination and epochs of EEG with artifacts frequency bands of the wavelet components: 0 to 2.33 Hz, 2.33 at 4.69 Hz, 4.69 at 9.38 Hz, 9.38-18.75 Hz, 18.75 at 37.5 Hz, 37.5 at 75 Hz, 75 at 150 Hz. The wavelet coefficients of each level greater than a threshold (average plus two standard deviations of non-contaminated epochs) take values of zero, which is equivalent to subtracting in time, point to point, the contaminant signal, associated with the wavelet coefficient that exceeds the threshold. In this same embodiment, a conditioning of the ECG signal is performed to determine the heart rate variability (HRV) and obtain a temporary series of intervals between beats. In this process, muscle activity noise, power line interference (50 or 60 Hz), baseline deviation and influence of the T wave are reduced. The energy of the QRS complex is distributed mainly between 5-15 Hz in the frequency spectrum. This is the bandpass desired and implemented in the digital filter.

The non-linear transformation applied corresponds to a point-to-point amplification of the filtered signal to obtain the square of it. The time series formed by the R peak intervals (RRI) constitute the biological signal for the measurement of HRV, from which indexes of autonomic activity of the patient during a surgical procedure are developed.

In the preferred embodiment of the present invention, a monitoring of biological signals is performed, particularly of the activity of the central and autonomic central systems corresponding to the extraction and identification of patterns of the information contained in the biological signals. Changes in the complexity of the EEG time series are monitored with the CBI constructed from sample entropy (SampEn) and permuted entropy (PE). Likewise, a quantification of the pattern corresponding to the Poincare-Lorenz dispersion graphs of the heart rate variability series is carried out by using descriptors SD1 and SD2.

[66] In the preferred embodiment of the present invention, the anesthetic depth pattern classification is carried out in accordance with the implementation of an artificial intelligence method and supervised learning of patterns in CBI, CVI, CSI, and NIBPm indexes. In this stage, the multilayer feedforward neural network is designed with an output layer in which a neuron is associated by state of anesthetic depth to classify with normalized exponential activation function, which is ideal for the type of output of the neural network. Also, regarding the inputs, the response is of exponential type with maximum value of 1. The neurons of the hidden layer have a hyperbolic tangent activation function and the number of neurons in this layer is chosen in a way that minimizes the classification error in the cross validation with 5 partitions. In this same preferred embodiment of the invention, once the respective cross-validation of the ANN has been trained and implemented and the generalization capacity has been analyzed, this is applied to determine the patient's status, being the best performance modality the one considering CBI, CVI and NIBPm (Table 2).

EXAMPLES

Practical embodiment of the Invention

The process of the invention was applied in sixty patients (aged between 18 and 65 years, American Society of Anesthesiologists ASA physical status I-III) scheduled for surgical procedures under general anesthesia at Universidad de La Sabana Teaching Hospital. The technique of total intravenous anesthesia was used through the target controlled infusion (TCI) pump (B. Braun Medical Inc., USA). The induction was carried out with 5 ng.ml-1 of remifentanil (Minto model) and 2.5 µg.ml-1 of propofol (Schneider model). The data acquisition starts 4 minutes before the induction and ends when the patient recovers the verbal response after the surgery is finished. The EEG signal was collected using a front entropy sensor and the S/5TM Collect software (Finland) at a sampling frequency of 300 Hz. The state entropy (SE) and response entropy (RE) tides were collected at 0.2 Hz.

The filtration technique that uses thresholds in wavelet components was implemented. The discrete stationary wavelet transform of 6 levels, with coiflet-3 as the mother wavelet, was applied at epochs of 1024 samples. The epochs to determine the threshold were taken from the base period of 4 minutes.

The signal was previously conditioned with a bandpass filter [0.5-47 Hz] to avoid noise in the power line (50 o 60 Hz) and, in general terms, high frequency contamination due to surgical instruments.

The SampEn and PE complexity measures were obtained from successive measurements of rectangular windows of 1024 samples.

The entropy parameters were post-processed and, subsequently, a mobile median filter of 5 entropy measures was applied in order to reduce dispersion and achieve a smoother response index that considers previous states of electroencephalography activity.

CBI, CVI and CSI were measured in the following anesthetic depth states defined by previously described clinical events, a.) Awake: Vigil—Ak, and recovery of verbal response—Rc.; b.) Light anesthesia: Light induction anesthesia—Li, Light recovery—Lr, Light dose—La; c.) General anesthesia: General anesthesia—Ga, one minute after the start of the surgery; d.) Deep anesthesia: identification of the EEG burst-suppression pattern (BSP) associated with deep anesthesia.

Anesthetic depth classification according to the process of the present invention The process of the invention was applied in sixty patients (aged between 18 and 65 years, American Society of Anesthesiologists ASA physical status I-III) scheduled for surgical procedures under general anesthesia at Universidad de La Sabana Teaching Hospital, in Bogotá, Colombia.

With the application of the process of the invention, an appropriate classification with cross-validation of 5 partitions was noted, of 99% for the awake state, with a confusion of 1% with the light anesthesia state, 0% of confusion with the states of general anesthesia and deep anesthesia.

In the determination of the state of light anesthesia there is a confusion of 4.64% with the state of awake patient, and of 7.95% with the state of general anesthesia. The respective confusion matrix for each one of the anesthetic depth states is shown in FIG. 9.

Figures 9, 10:
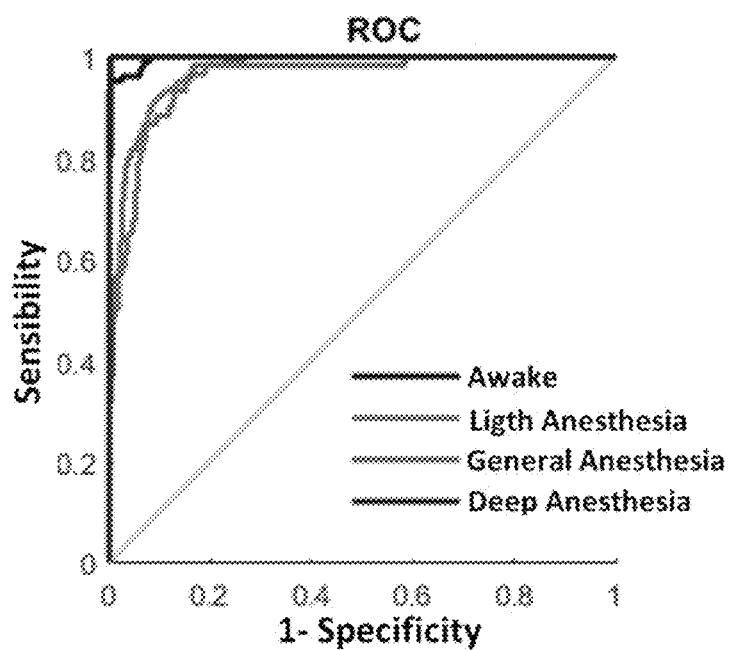
FIG. 9 is a table of Confusion matrix for the best performance classifier.
FIG. 10 is a graph illustration of Receiver Operating Characteristic (ROC) curve, Sensitivity, 1-Specificity.

The Receiver Operating Characteristic (ROC) curve, the True Positive Rate (TPR) and the False Positive Rate (FPR) are shown in FIG. 10.

We claim:

1. A method for classifying anesthetic depth, comprising the steps of:
   a. collection of biological signals from a patient, conditioning of said signals, monitoring of activity of the Central Nervous System (CNS) and Autonomous Nervous system (ANS), and classification of patterns in anesthetic depth, wherein the collection of biological signals includes the collection of an Electroencephalogram (EEG) signal, an Electrocardiogram (ECG) signal, and mean non-invasive blood pressure (NIBPm);
   b. conditioning the biological signals by eliminating factors external to the patient and biological noise, applying digital filters and a wavelet transform method;
   c. monitoring of the CNS and ANS activity, by measuring the complexity of the waveform of the EEG signal with the Complexity Brainwave Index (CBI index), and integration with Heart Rate Variability (HRV) indices, Cardiac vagal Index (CVI), and Cardiac Sympathetic Index (CSI) derived from the ECG signal;
   d. classification of patterns associated with the Central Nervous System, including the CBI, and Autonomic Nervous System, including the CVI, CSI, and NIBPm, in response to clinical events during the surgical procedure, pattern classifiers are designed and finally the patient's status is classified in anesthetic depth.

2. The method for classifying anesthetic depth according to claim 1, wherein the collection of biological signals is performed by recording brain electrical activity (EEG) using a unilateral reference sensor with an exploring electrode and a reference electrode, achieving a trace at a sampling frequency between 100 and 300 Hz, and wherein the recording of cardiac electrical activity (ECG) uses a setup with three leads, at a sampling frequency between 100 and 300 Hz, and the recording of Non-Invasive Arterial Pressure, and is performed at intervals of 150 s.

3. The method for classifying anesthetic depth according to claim 1, wherein the conditioning of the biological signals is carried out by applying a digital filter for EEG ([0.5-47 Hz]) and for ECG ([5-15 Hz]) and then, based on the threshold of the coefficients of the wavelet coiflet-3 transform from 4 to 8 levels, decomposed into frequency ranges according to the levels.

4. The method for classifying anesthetic depth according to claim 1, wherein
the activity monitoring of the CNS and ANS, corresponds to the extraction and identification of patterns of information contained in the EEG biological signals and ECG, which are monitored through the CBI, CVI, CSI indices, wherein the CBI is obtained from calculating the sample entropy (SampEn) and permuted (PE) entropy of the EEG signal, and by quantifying the pattern corresponding to a Poincaré-Lorenz dispersion graphs of the heart rate variability series using SD1 and SD2 descriptors.

5. The method for classifying anesthetic depth according to claim 1, wherein
the classification implements a multilayer feedforward neural network (ANN) designed with an output layer in which a neuron is associated by state of anesthetic depth to classify with a normalized exponential activation function, and where the ratio of the inputs to the response is of the exponential type with a maximum value equal to 1, and wherein once the respective cross-validation of the ANN has been trained and implemented, it is applied to determine the patient's status:
  a. awake: wakefulness—Ak, and recovery of verbal response—Rc;
  b. light anesthesia: light anesthesia in induction—Li, light recovery Lr, light dose (La);
  c. general anesthesia: general anesthesia—Ga, one minute after the start of the surgical procedure;
  d. deep anesthesia: identification of the pattern in the EEG burst-suppression (BSP) associated with deep anesthesia;
  wherein the best performance is the one that considers patterns in the CBI, CVI and NIBPm indices.

6. The method for classifying anesthetic depth according to claim 1, wherein the classification is performed by the implementation of an ANN cross-validation, and the patient's status is determined in: a.) Awake: Vigil—Ak, and recovery of verbal response—Rc; b.) Light Anesthesia: Light induction anesthesia—Li, Light recovery—Lr, Light dose—La; c.) General Anesthesia: General anesthesia—Ga, one minute after the start of the surgery; d.) Deep anesthesia: identification of the EEG burst-suppression pattern (BSP) associated with deep anesthesia.

7. The method for classifying anesthetic depth, according to claim 3, wherein the threshold components Wavelet technique has a parent coiflet-3 function that imitates the signal of an eye blink.

8. The method for classifying anesthetic depth, according to claim 1, wherein the classification is performed on a neural network trained with a scaled conjugate gradient backpropagation algorithm, and the performance function during training corresponds to cross entropy.

* * * * *